(12) United States Patent
Nevins et al.

(10) Patent No.: US 11,610,378 B1
(45) Date of Patent: *Mar. 21, 2023

(54) SYSTEM AND METHOD FOR LOCATION DETERMINATION USING A MIXED REALITY DEVICE AND MULTIPLE IMAGING CAMERAS

(71) Applicants: Russell Todd Nevins, Las Vegas, NV (US); David Jon Backstein, Toronto (CA); Bradley H. Nathan, Toronto (CA)

(72) Inventors: Russell Todd Nevins, Las Vegas, NV (US); David Jon Backstein, Toronto (CA); Bradley H. Nathan, Toronto (CA)

(73) Assignees: Russell Todd Nevins, Las Vegas, NV (US); David Jon Backstein, Ontario (CA); Bradley H. Nathan, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/730,069

(22) Filed: Apr. 26, 2022

Related U.S. Application Data (62) Division of application No. 17/722,265, filed on Apr. 15, 2022.

(Continued)

(51) Int. Cl.
*G06T 19/00* (2011.01)
*H04N 5/247* (2006.01)
(Continued)

(52) U.S. Cl.
CPC .......... *G06T 19/006* (2013.01); *A61B 90/361* (2016.02); *A61B 90/37* (2016.02);
(Continued)

(58) Field of Classification Search
None
See application file for complete search history.

(56) References Cited

U.S. PATENT DOCUMENTS 7,331,929 B2   2/2008   Morita et al.
7,812,815 B2   10/2010  Banerjee
(Continued)

FOREIGN PATENT DOCUMENTS

CN   107430437 A   12/2017
CN   110430809 A   11/2019
(Continued)

OTHER PUBLICATIONS

Microsoft HoloLens & Mixed /Reality Healthcare Industry Deck, unknown author, at least as early as Oct. 14, 2019.
(Continued)

*Primary Examiner* — Steven Z Elbinger
(74) *Attorney, Agent, or Firm* — Morris O'Bryanyt Compagni Cannon, PLLC (57) ABSTRACT

A system and method for determining a location for a surgical jig in a surgical procedure includes providing a mixed reality headset, a 3D spatial mapping camera, an infrared or stereotactic camera, and a computer system configured to transfer data to and from the mixed reality headset and the 3D spatial mapping camera. The system and method also include attaching a jig to a bone, mapping the bone and jig using the 3D spatial mapping camera, and then identifying a location for the surgical procedure using the computer system. Then the system and method use the mixed reality headset to provide a visualization of the location for the surgical procedure.

30 Claims, 8 Drawing Sheets

Related U.S. Application Data (60) Provisional application No. 63/252,074, filed on Oct. 4, 2021.

(51) Int. Cl.
*H04N 13/25* (2018.01)
*H04N 13/332* (2018.01)
*A61B 90/00* (2016.01)
*G02B 27/01* (2006.01)
*G06T 7/70* (2017.01)
*A61B 90/50* (2016.01)

(52) U.S. Cl.
CPC .......... *G02B 27/0172* (2013.01); *G06T 7/70* (2017.01); *H04N 5/247* (2013.01); *H04N 13/25* (2018.05); *H04N 13/332* (2018.05); *A61B 2090/365* (2016.02); *A61B 2090/397* (2016.02); *A61B 2090/3916* (2016.02); *A61B 2090/3937* (2016.02); *A61B 2090/502* (2016.02); *G02B 2027/0138* (2013.01); *G02B 2027/0174* (2013.01); *G06T 2200/04* (2013.01); *G06T 2207/10012* (2013.01); *G06T 2207/10048* (2013.01); *G06T 2207/30008* (2013.01); *G06T 2207/30204* (2013.01); *G06T 2210/41* (2013.01)

(56) References Cited

U.S. PATENT DOCUMENTS

| | | | |
|---|---|---|---|
| 8,123,754 B2 | 2/2012 | Siebel | |
| 8,560,047 B2 | 10/2013 | Haider et al. | |
| 8,876,830 B2 | 11/2014 | Hodorek | |
| 8,954,181 B2 | 2/2015 | MacLeod | |
| 8,956,165 B2 | 2/2015 | Kurenov | |
| 9,563,266 B2 | 2/2017 | Banerjee | |
| 9,730,713 B2 | 8/2017 | Park | |
| 9,861,446 B2 | 1/2018 | Lang | |
| 9,892,564 B1 | 2/2018 | Cvetko et al. | |
| 9,978,141 B2 | 5/2018 | Stolka et al. | |
| 9,980,780 B2 | 5/2018 | Lang | |
| 10,016,243 B2 | 7/2018 | Esterberg | |
| 10,108,266 B2 | 10/2018 | Banerjee | |
| 10,159,530 B2 | 12/2018 | Lang | |
| 10,194,990 B2 | 2/2019 | Amanatullah | |
| 10,220,181 B2 | 3/2019 | Giap | |
| 10,241,569 B2 | 3/2019 | Lanman | |
| 10,278,777 B1 | 5/2019 | Lang | |
| 10,285,765 B2 | 5/2019 | Sachs | |
| 10,286,179 B2 | 5/2019 | Giap | |
| 10,292,768 B2 | 5/2019 | Lang | |
| 10,368,947 B2 | 8/2019 | Lang | |
| 10,401,954 B2 | 9/2019 | Koker | |
| 10,405,873 B2 | 9/2019 | Amiot | |
| 10,405,927 B1 | 9/2019 | Lang | |
| 10,437,335 B2 | 10/2019 | Daniels | |
| 10,437,339 B2 | 10/2019 | Banerjee | |
| 10,602,114 B2 | 3/2020 | Casas | |
| 10,672,288 B2 | 6/2020 | Ribeira et al. | |
| 10,716,643 B2 | 7/2020 | Justin et al. | |
| 10,888,399 B2 | 1/2021 | Kopelman et al. | |
| 10,980,601 B2 | 4/2021 | Yang et al. | |
| 11,045,263 B1 | 6/2021 | Nevins et al. | |
| 11,172,990 B2 | 11/2021 | Lang | |
| 2005/0251030 A1 | 11/2005 | Azar et al. | |
| 2008/0183179 A1 | 7/2008 | Siebel | |
| 2009/0163923 A1 | 6/2009 | Flett | |
| 2014/0222462 A1 | 8/2014 | Shakil et al. | |
| 2016/0191887 A1 | 6/2016 | Casas | |
| 2016/0261300 A1* | 9/2016 | Fei | H04N 5/33 |
| 2017/0245781 A1 | 8/2017 | Kay | |
| 2017/0258526 A1* | 9/2017 | Lang | A61B 34/74 |
| 2017/0312032 A1 | 11/2017 | Amanatullah et al. | |
| 2017/0367766 A1 | 12/2017 | Mahfouz | |
| 2017/0367771 A1 | 12/2017 | Tako et al. | |
| 2018/0049622 A1* | 2/2018 | Ryan | A61B 34/10 |
| 2018/0090029 A1 | 3/2018 | Fisher | |
| 2018/0098813 A1 | 4/2018 | Nesichi | |
| 2018/0116728 A1 | 5/2018 | Lang | |
| 2018/0240276 A1 | 8/2018 | He et al. | |
| 2018/0348876 A1 | 12/2018 | Banerjee | |
| 2019/0038362 A1 | 2/2019 | Nash et al. | |
| 2019/0076198 A1 | 3/2019 | Berend | |
| 2019/0110842 A1 | 4/2019 | Lang | |
| 2019/0142520 A1 | 5/2019 | VanDyken | |
| 2019/0149797 A1 | 5/2019 | Casas | |
| 2019/0216562 A1 | 7/2019 | Sachs | |
| 2019/0262078 A1 | 8/2019 | Lang | |
| 2019/0366030 A1 | 12/2019 | Giap et al. | |
| 2019/0380792 A1 | 12/2019 | Poltaretskyi et al. | |
| 2020/0000527 A1 | 1/2020 | Cazal | |
| 2020/0037043 A1 | 1/2020 | Phillips et al. | |
| 2020/0078100 A1 | 3/2020 | Weinstein et al. | |
| 2020/0107003 A1 | 4/2020 | Phillips et al. | |
| 2020/0275976 A1 | 9/2020 | McKinnon | |
| 2020/0275988 A1 | 9/2020 | Johnson et al. | |
| 2020/0302694 A1 | 9/2020 | Flexman et al. | |
| 2020/0360093 A1 | 11/2020 | Khan et al. | |
| 2020/0375666 A1 | 12/2020 | Murphy, M.D. | |
| 2021/0093329 A1 | 4/2021 | Poltaretskyi et al. | |
| 2021/0093333 A1* | 4/2021 | Chappuis | A61B 34/30 |
| 2021/0093391 A1 | 4/2021 | Poltaretskyi et al. | |
| 2021/0093413 A1 | 4/2021 | Poltaretskyi et al. | |
| 2021/0142508 A1* | 5/2021 | Azimi | G02B 27/017 |
| 2021/0228286 A1 | 7/2021 | Moghaddam et al. | |
| 2021/0228308 A1 | 7/2021 | Berger et al. | |
| 2021/0244481 A1 | 8/2021 | Jaramaz et al. | |
| 2022/0047279 A1 | 2/2022 | Nevins et al. | |
| 2022/0051483 A1 | 2/2022 | Nevins et al. | |

FOREIGN PATENT DOCUMENTS

| | | |
|---|---|---|
| CN | 110431636 A | 11/2019 |
| DE | 10103922 A1 | 8/2002 |
| DE | 102015212352 A1 | 1/2017 |
| EP | 3113682 A1 | 1/2017 |
| GB | 2570758 A | 7/2019 |
| JP | 2020515891 A | 5/2020 |
| WO | 2007108776 A2 | 9/2007 |
| WO | 2012033739 A2 | 3/2012 |
| WO | 2015134953 A1 | 9/2015 |
| WO | 2017066373 A1 | 4/2017 |
| WO | 2018007091 A1 | 1/2018 |
| WO | 2018132804 A1 | 7/2018 |
| WO | 2018175971 A1 | 9/2018 |
| WO | 2019051080 A1 | 3/2019 |
| WO | 2019245870 A1 | 12/2019 |
| WO | 2020033568 A2 | 2/2020 |
| WO | 2020037308 A1 | 2/2020 |
| WO | 2020047051 A1 | 3/2020 |
| WO | 2020145826 A1 | 7/2020 |
| WO | 2021094354 A1 | 5/2021 |

OTHER PUBLICATIONS

Kaluschke et al., HIPS—A Virtual Reality Hip Prosthesis Implantation Simulator, retrieved at https://www.reasearchgate.net/publication/327329265, upload date Sep. 3, 2018 DOI: 10.1109/VR.2018.8446370.

Vaughan et al., Does Virtual-Reality Training on Orthopaedic Simulators Improve Performance in the Operating Room? Science and Information Conference 2015, Jul. 28-30, 2015, London, UK; retrieved at https://www.researchgate.net/publication/284415791; DOI: 10.1109/SAI.2015.7237125.

Patently Apple—Apple Reveals a Mixed Reality Headset that Uses a Direct Retinal Projector System With Holographic Lenses, retrieved at https://www.patentlyapple.com/patently-apple/2019/09/apple-reveals-a-mixed-reality-headset-that-uses-a-direct-retinal-projector-system-with-hologra . . . ; posted date Sep. 19, 2019.

(56) References Cited

OTHER PUBLICATIONS

Virtual Reality System Helps Surgeons, Reassures Patients, retrieved at https//medicalgiving.stanford.edu/news/virtual-reality-system-helps-surgeons-reassures-patients.html, retrieved date Oct. 24, 2019.

Immersive Touch Launches the First Virtual Reality Integrated Suite for Surgical Planning, retrieved at https://spinalnewsinternational.com/immersivetouch-virtual-reality-suite, dated Oct. 5, 2018.

Daley, Sam, The Cutting Edge: 10 Companies Bringing Virtual Reality & AR to the OR, retrieved at https://builtin.com/healthcare-technology/augmented-virtual-reality-surgery, dated Jul. 5, 2019.

Barad, Justin, Virtual and Augmented Reality Can Save Lives by Improving Surgeons' Training, retrieved at https://www.statnews.com/2019/08/16/virtual-reality-improve-surgeon-training, dated Aug. 16, 2019.

Levin et al., The Future of Virtual Reality in Ophthalmology Is Already Here, retrieved at https://www.aao.org/young-ophthalmologists/yo-info/article/future-of-virtual-reality-in-ophthalmology, dated Aug. 16, 2019.

Vaughan et al., A Review of Virtual Reality Based Training Simulators for Orthopaedic Surgery, retrieved at https://www.researchgate.net/publication/283727217, posted date Feb. 22, 2019, DOI: 10.1016/j.medengphy.2015.11.021.

LexInnova Patent Landscape Analysis, Virtual Reality, unknown author, copyright date of 2015.

Virtual & Augmented Reality Are You Sure it Isn't Real? Kathleen Boyle, CFA, Managing Editor, Citi GPS dated Oct. 2016.

New Apple patent filing shows a mixed reality headset that tracks your whole face, Jul. 22, 2019, (downloaded Jul. 1, 2020 at https://www.theverge.com/2019/7/22/20705158/apple-mixed-reality-headset-ar-glasses-patent-application-face-tracking), 2 pages.

"Augmented and virtual reality in surgery-the digital surgical environment: application, limitations and legal pitfalls," accessed at https://www.ncbi.nlm.nih.gov/pmc/articles/PMC5220044/, visited on Jul. 4, 2020. 12 pages.

"The impact of Web3D technologies on medical education and training," Science Direct, accessed at https://www.sciencedirect.com/science/article/pii/S0360131505000825, visited on Jul. 4, 2020, 11 pages.

"Mixed Reality with HoloLens: Where Virtual Reality Meets Augmented Reality in the Operating Room," accessed at https://www.ingentaconnect.com/content/wk/prs/2017/00000140/00000005/art00063, visited on Jul. 4, 2020, 1 page.

"Virtual Reality Simulation in Neurosurgery: Technologies and Evolution," Abstract, accessed at https://academic.oup.com/neurosurgery/article-abstract/72/suppl_1/A154/2417686, visited on Jul. 4, 2020, 2 pages.

Katanacho, Manuel, Wladimir De la Cadena, and Sebastian Engel. "Surgical navigation with QR codes: Marker detection and pose estimation of QR code markers for surgical navigation." Current Directions in Biomedical Engineering 2.1 (2016): 355-358.

\* cited by examiner

SYSTEM AND METHOD FOR LOCATION DETERMINATION USING A MIXED REALITY DEVICE AND MULTIPLE IMAGING CAMERAS

CROSS-REFERENCE TO RELATED APPLICATIONS

This application is a divisional of non-provisional U.S. patent application Ser. No. 17/722,265, filed on Apr. 15, 2022, which claims the benefit of U.S. Provisional Application No. 63/252,074, filed Oct. 4, 2021, which are hereby incorporated by reference herein in their entirety, including but not limited to those portions that specifically appear hereinafter, the incorporation by reference being made with the following exception: In the event that any portion of the above-referenced applications are inconsistent with this application, this application supercedes said above-referenced applications.

STATEMENT REGARDING FEDERALLY SPONSORED RESEARCH OR DEVELOPMENT

Not applicable.

BACKGROUND

1. The Field of the Present Disclosure

The present disclosure relates generally to surgical systems and methods of facilitating the efficiency and accuracy of implanting surgical prostheses using mixed reality and 3D spatial mapping devices.

2. Description of Related Art

In traditional implant surgeries, e.g., knee replacements, a surgeon will utilize a metal jig that is used as a drilling or cutting guide to make the necessary corresponding cuts and holes in the bone of the knee to facilitate placement and attachment of the implant to the bone. However, these metal jigs must be stocked in a variety of different sizes to accommodate different needs and sizes of patients. Accordingly, significant stocks of metal jigs must be stored and sterilized. Additionally, use of such metal jigs in surgical applications is not an exact science and requires the surgeon to manually attach the metal jig to a corresponding bone for use as a drill or cutting guide, which necessarily introduces some inaccuracies.

In knee replacement surgery, the femoral and tibial implants are designed to be surgically implanted into the distal end of the femur and the proximal end of the tibia, respectively. The femoral implant is further designed to cooperate with the tibial implant in simulating the articulating motion of an anatomical knee joint.

These femoral and tibial implants, in combination with associated ligaments and muscles, attempt to duplicate natural knee motion as well as absorb and control forces generated during the range of flexion. In some instances, such as when the femoral or tibial implant becomes excessively worn at the joint, it may be necessary to replace or modify an existing the femoral and/or tibial implant. Such replacements are generally referred to as revision implants.

To prepare a femur and tibia for such a knee replacement operation and to form an engagement with femoral and tibial implants, the femur and tibia bones must be cut in very specific and precise ways and at very specific and precise angles and locations so that the prepared bones will properly engage with and can be properly secured to the corresponding implants. In order to properly cut the femur and tibia, a surgeon traditionally uses a jig or surgical cutting guide as is known to those skilled in the field. For each bone to be cut, a jig is temporarily attached or secured to the bone, such that slots or guides in the jig facilitate the alignment of cutting tools used to make precise cuts necessary for securing a corresponding implant.

The phrase "jig" as used herein, refers broadly to a surgical cutting guide that may be configured and arranged to be fixed or attached to a bone, or secured adjacent to a bone or other tissue, to be cut by a surgeon and identify a relative location, angle and/or cutting plane that a surgeon should cut or drill on the adjacent bone or tissue, as known in the art. A jig may include predetermined slots, apertures, holes and/or cutting surfaces to identify where a surgeon should cut or drill the adjacent bone or tissue, wherein such cuts or holes may correspond to a shape of a surgical implant that may be attached to the cut bone or tissue. A "cutting surface" may refer to a guide edge for guiding the path of a cutting instrument.

Conventional jigs are typically made of a metal alloy and, due to the precise tolerances at which these jigs must be machined, are quite expensive, ranging as high as $40,000-$50,000 in some cases. These metal jigs must also be stored and reused, which adds additional cost and utilizes space resources. Additionally, jigs of various sizes must be kept on hand to accommodate patients of different sizes and with different needs.

Therefore, there is a need for a system that can utilize a less expensive jig, such as a plastic jig, that could be made easily and on demand, while maintaining the required tolerances and enable the same accuracy in use in a surgical procedure.

In other conventional embodiments, holographic jigs, also referred to as virtual jigs, have been used to enable a surgeon to visualize the positioning and proper sizing of a jig to a bone. However, in use, when the surgeon attempts to superimpose a physical jig over the virtual jig to attach it to a bone to make the required bone cuts, the physical jig will impair the view of the virtual or holographic jig, making it difficult to utilize the holographic jig to accurately place the physical jig.

Accordingly, there is a need for a system and method of utilizing a virtual or holographic jig or surgical instrument that can facilitate increased accuracy and precision of required or desired bone cuts.

The phrase "virtual jig" or "holographic jig" as used herein, shall thus refer broadly to any visualization or visual rendering or projection representing an actual physical jig, having all, or mostly all, of the same visual characteristics of the physical jig, including size and shape, as known in the art.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims. Any discussion of documents, acts, materials, devices, articles or the like which has been included in the present specification is not to be taken as an admission that any or all of these matters form part of the prior art base, or were common general knowledge in the field relevant to the present disclosure as it existed before the priority date of each claim of this application.

BRIEF DESCRIPTION OF THE DRAWINGS

The features and advantages of the disclosure will become apparent from consideration of the subsequent detailed description presented in connection with the accompanying drawings in which.

DETAILED DESCRIPTION

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the terms "virtual," and "hologram" are used interchangeably, and grammatical equivalents thereof are inclusive or open-ended terms that do not exclude additional, unrecited elements or method steps. These terms are used to describe visual representations of an actual physical device or element, having all, or mostly all, of the same visual characteristics of the physical device, including size and shape.

Applicant has discovered a novel system and method for generating and using a virtual jig, or virtual instrument, in a surgical procedure, for example, in a knee or tibial implant procedure, or other desired surgical procedure.

The phrase "virtual system," as used herein, shall refer broadly to any system capable of generating or creating a simulated or virtual rendering or projection of physical or structural features identical or substantially identical to an actual physical device, instrument or other physical structure, as known in the art. A virtual system may also include a device, mechanism, or instrument capable of projecting or displaying the desired simulated or virtual rendering or projection of physical or structural features identical or substantially identical to an actual physical device. A virtual system may also enable a user to manipulate, move and/or modify the simulated or virtual rendering or projection.

The phrase "mixed or augmented reality system," as used herein, shall refer broadly to any system capable of generating or creating a simulated or virtual rendering or projection of physical or structural features identical or substantially identical to an actual physical device, instrument or other physical structure, as known in the art. A mixed or augmented reality system may also include a device, mechanism, or instrument capable of projecting or displaying the desired a simulated or virtual rendering or projection of physical or structural features identical or substantially identical to an actual physical device overlaid or concurrently with actual physical structures, mechanism or devices in reality, thus incorporating the virtual rendering or projection in real world settings with actual physical element. A mixed or augmented reality system may also enable a user to manipulate, move and/or modify the simulated or virtual rendering or projection.

The phrase "mixed or augmented reality instrument," as used herein, shall refer broadly to any device, mechanism or instrument used in a mixed or augmented reality system, including a device capable of generating or creating a simulated or virtual rendering or projection of physical or structural features identical or substantially identical to an actual physical device, instrument or other physical structure, as known in the art. A mixed or augmented reality instrument may also be capable of projecting or displaying the desired a simulated or virtual rendering or projection of physical or structural features identical or substantially identical to an actual physical device overlaid or displayed concurrently with actual physical structures, mechanism or devices in reality, thus incorporating the virtual rendering or projection in real world settings with actual physical elements. A mixed or augmented reality instrument may also enable a user to manipulate, move and/or modify the simulated or virtual rendering or projection.

The phrase "holographic representation," as used herein, shall refer broadly to a visualization or visual rendering or projection representing an actual physical device or element, having all, or mostly all, of the same visual characteristics of the corresponding physical device or element, including size and shape, as known in the art.

Figure 1:
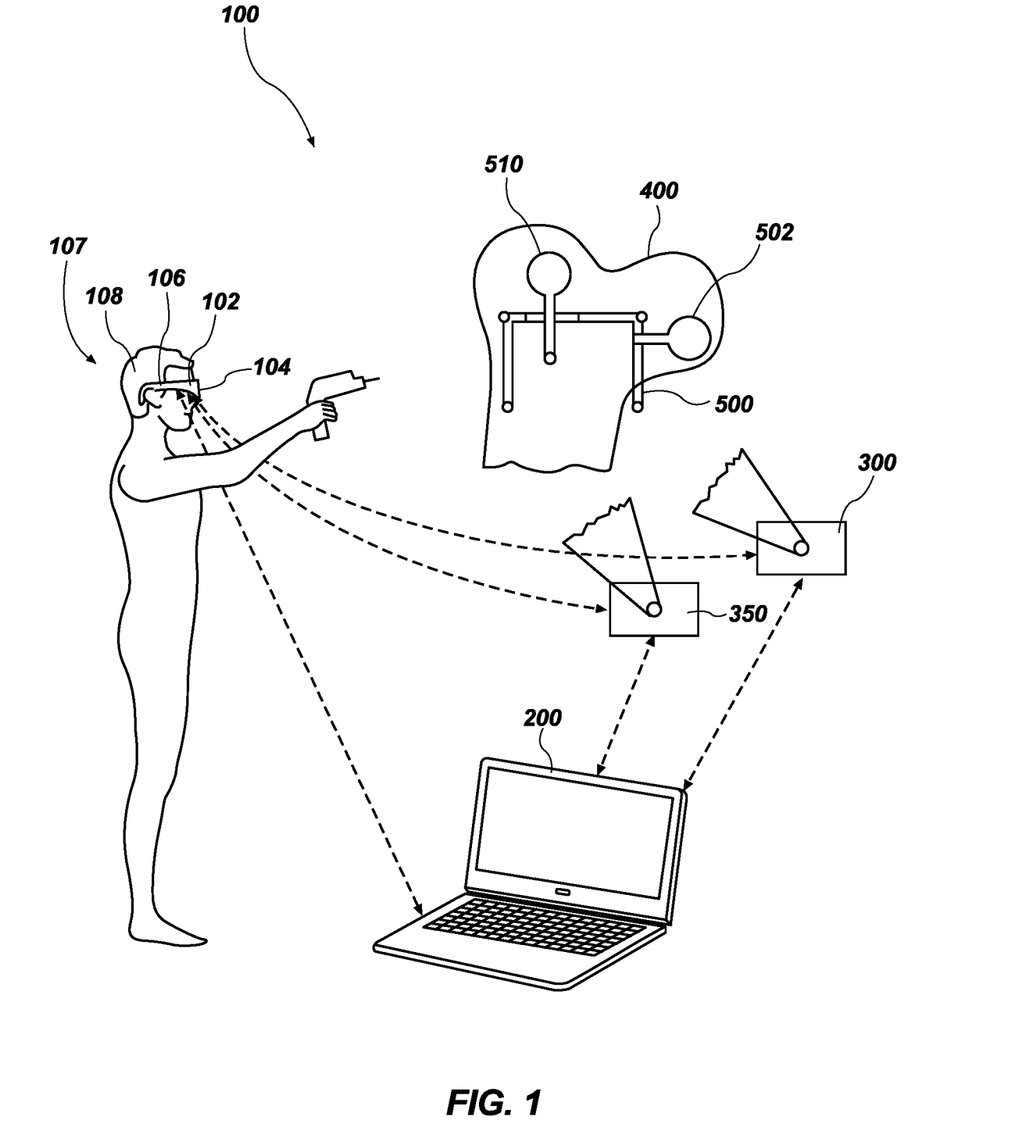
FIG. 1 is a schematic rendering of a mixed reality system of the present disclosure.

Referring now to the drawings, FIG. 1, in a disclosed embodiment, illustrates a mixed or augmented system 100, which can be used to produce, or display, a desired mixed or augmented reality instrument, such as a virtual jig or cutting guide in a display to a surgeon or user, or stated another way, that is visible and manipulatable by a surgeon or user. The mixed or augmented reality system 100 may also enable a user to activate or deactivate, in full or in part, the virtual instrument or instruments, making a virtual instrument appear or disappear, as, for example, may be desired in a mixed reality assisted surgery.

The mixed or augmented reality system 100 may include a mixed or augmented reality headset 102 which may include a transparent or mostly transparent viewer 104 which can be suspended or positioned in front of a user's eyes. The headset 102 may include a headband 106 attached to the viewer 104, which may be used to secure the headset 102 to a user's head 108, thereby securing the viewer 104 in place in front of the user's eyes.

The transparent viewer 104 may be configured to project, or otherwise make viewable, on an interior surface of the viewer 104, a holographic image or images, such as a virtual device, for example, a virtual cutting guide, which may be positionally manipulated by the user, surgeon, third party or remote system, such as a remote computer system. The headset 102 may be configured to view holographic images or, alternatively, the holographic images may be turned off and the user wearing the headset 102 may be able to view the surrounding environment through the transparent viewer 104 without obstruction. As such, a user, such as a surgeon for example, can wear the mixed or augmented reality headset 102 and then can choose to activate a holographic image to aide in facilitating a surgical procedure and then shut off the holographic image in order to perform the surgical procedure in a visually un-obscured manner.

One embodiment of the disclosed headset 102 utilizes a Microsoft Corporation product, known as the HoloLens® mixed or augmented reality system. Other suitable mixed or augmented reality systems for generating virtual images viewable by a user or surgeon may also be employed. Thus, the headset 102 may be a conventional "off the shelf" product with a built-in platform that enables all of the features described herein with respect to the headset 102. Furthermore, the headset 102, such as Microsoft's HoloLens® product, can be loaded or preloaded with all desired or required virtual instruments, including virtual jigs or surgical cutting guides, virtual drill bits, and/or a virtual target which can identify relative locations of a plurality of holes to be drilled by a surgeon to facilitate the fastening of a jig or other device onto a desired bone at the proper desired location, and any other desired virtual instruments or holograms. The Microsoft HoloLens® product and its capabilities and features, or any suitable mixed or augmented reality system, such as is described herein with respect to the headset 102, are known to those skilled in the art.

The mixed reality system 100 may also include a computer or computer system 200 having enabling software to communicate with the headset 102, by both receiving information from the headset 102 and transmitting data and images to the headset 102. It is therefore to be understood, by way of the circuit diagram and dashed lines shown in FIG. 1, that headset 102 is electronically connected to the computer system 200 and a 3D spatial mapping camera 300 and another imaging camera or infrared camera 350. In alternative embodiments, the imaging camera 350 may be a stereotactic or stereotaxic device or camera, which may also be represented by reference numeral 350, as the included figures and drawings are schematic in nature and do not disclose the mechanical or electrical details of the infrared camera or the stereotactic devices, as those details are known by those skilled in the art. The 3D spatial mapping camera 300 and infrared or stereotactic camera 350 are electronically connected to the headset 102 and the computer system 200, as shown in the circuit diagram and dashed lines shown in FIG. 1. While the 3D spatial mapping camera 300 and infrared or stereotactic camera 350 may be electronically connected to the headset 102, the 3D spatial mapping camera 300 and infrared or stereo tactic camera 350 may be separate from and not mechanically connected to the headset 102.

The mixed reality system 100 may also include a 3D spatial mapping camera 300 and an infrared or stereotactic camera 350. One embodiment of the disclosed spatial mapping camera 300 may be a product created and manufactured by Microsoft Corporation, known as the Azure Kinect, or any suitable 3D spatial mapping camera capable of continuous 3D mapping and transition corresponding 3D images, such as bones, anatomy, or other desired 3D objects. The spatial mapping camera 300 may be a conventional "off the shelf" product with a built-in platform that enables all of the features described herein with respect to the spatial mapping camera 200. Furthermore, the spatial mapping camera 200, such as Microsoft's Azure Kinect® product, can be loaded or preloaded with all necessary software to enable wireless communication between the spatial mapping camera 300 and the computer system 200 and/or the headset 102. Microsoft's Azure Kinect® product and its capabilities and features, or any suitable 3D spatial mapping camera such as is described herein with respect to the spatial mapping camera 300, are known to those skilled in the art.

The spatial mapping camera 300 may include sensor software development kits for low-level sensor and device access, body tracking software development kits for tracking bodies or objects in 3D, and speech cognitive services software development kits for enabling microphone access and cloud-based or wireless speech services.

Additionally, the spatial mapping camera 300 may include the following features: depth camera access and mode control (a passive IR mode, plus wide and narrow field-of-view depth modes); RGB camera access and control (for example, exposure and white balance); a motion sensor (gyroscope and accelerometer) access; synchronized depth-RGB camera streaming with configurable delay between cameras; external device synchronization control with configurable delay offset between devices; camera frame metadata access for image resolution, timestamp, etc.; and device calibration data access.

The spatial mapping camera 300 may also include: software development kits that enable a viewer tool to monitor device data streams and configure different modes; a sensor recording tool and playback reader API that uses the Matroska container format, as known to those of ordinary skill in the field; a library and runtime to track bodies in 3D when used with the spatial mapping camera 300; an anatomically correct skeleton for each partial or full body; a unique identity for each body; ability to track bodies over time; and speech recognition and translation capabilities, such as, speech-to-text, speech translation and text-to-speech.

In one disclosed embodiment, the imaging camera 350 comprises an infrared camera 350, which may be any suitable infrared camera capable of continuous infrared imaging, such as bones, anatomy, or other desired 3D objects. The infrared imaging camera 350 may be a conventional "off the shelf" product with a built-in platform that enables all of the features described herein with respect to the infrared camera 200. Furthermore, the infrared camera 350 can be loaded or preloaded with all necessary software to enable wireless communication between the infrared imaging camera 350 and the computer system 200 and/or the headset 102. The infrared camera 350 may be any suitable infrared camera such as is described herein with respect to the infrared imaging camera 350, are known to those skilled in the art. The infrared imaging camera 350, as known in the art, may provide or identify desired coordinates in a 3D space, thus providing accurate and detailed location determination in a desired 3D space.

In another disclosed embodiment the imaging camera 350 comprises a stereotactic camera 350, which may be any suitable stereotactic camera capable of continuous stereotaxic imaging, such as bones, anatomy, or other desired 3D objects. The stereotactic imaging camera 350 may be a conventional "off the shelf" product with a built-in platform that enables all of the features described herein with respect to the stereotactic camera 200. Furthermore, the stereotactic imaging camera 350 can be loaded or preloaded with all necessary software to enable wireless communication between the stereotactic imaging camera 350 and the computer system 200 and/or the headset 102. The stereotactic imaging camera 350 may be any suitable stereotactic camera such as is described herein with respect to the stereotactic camera 350, are known to those skilled in the art. The stereotactic imaging camera 350, as known in the art, may provide or identify desired coordinates in a 3D space, thus providing accurate and detailed location determination in a desired 3D space.

The headset 102, computer system 200, spatial mapping camera 300, and infrared or stereotactic imaging camera 350, may be programmed and configured to enable a surgeon 107 to see and manipulate a virtual, or holographic target or jig, or visual representation of a jig, with respect a patient's bone 400, anatomical, or any other desired location, which may receive a surgical implant. The headset 102, computer system 200 and spatial mapping camera 300 may communicate with one another via a local network connection, Wi-Fi, Bluetooth®, or any other known wireless communication signal.

Specifically, the spatial mapping camera 300, which may be programed to communicate with the computer system 200 having enabling software, may utilize such enabling software to combine coordinate data or information from the infrared camera or sterotactic camera 350 with the imaging data from the spatial mapping camera 300 to digitally map the bone 400 and/or jig 500, or other desired anatomy, producing a first digital map, to help identify the proper location for fastening a jig, or other device, to the bone 400, prior to cutting the knee.

The spatial mapping camera 300 differs from traditional imaging, such as an MRI, CT scan, x-ray or the like, in many ways. For example, the spatial mapping camera 300 may be mounted, fixedly or moveably, in an operating room, thus giving the most up-to-date mapping information possible. The spatial mapping camera 300 may also continuously map the surface and 3D contours of the bone 400 to provide the surgeon 107 with real-time feedback, imaging data, and information to make the proper drill holes, cuts, or other preparations on the bone 400, before, during, and/or after any given procedure.

The computer system 200 with enabling software may utilize and overlay or superimpose the respective images, coordinates, or imaging information or display data from both the spatial mapping camera 300 and the infrared or stereotactic camera, to identify coordinates or key features of the bone 400 and or jig 500, or other desired anatomy, or may identify key features of a desired location for a surgical procedure, to help identify the proper location for fastening a jig, or other device, to the bone 400, prior to cutting the knee. The computer system 200 may then identify coordinates of the location of the jig 500 using the stereotactic camera 350 and identify a location for the surgical procedure by using the computer system 200 to superimpose a mapping image from the 3D spatial mapping camera 300 and a coordinates based image from the infrared or stereotactic camera 350, to produce a second digital map.

The imaging data or information from the spatial mapping camera 300 may provide contour mapping of the surrounding bone 400 or other desired 3D space, while the infrared or stereotactic camera 350 can provide coordinates that more accurately identify exact or substantially exact locations in three dimensions. Thus, the combination of the superimposed images from the spatial mapping camera 300 and the infrared or stereotactic camera 350 can provide more accurate location information than either camera 300 or 350 alone.

Additionally, the use of the combination of the spatial mapping camera 300 and the infrared or stereotactic camera 350 can enable the cameras 300 and 350 to be placed or fixed at a location that is further from the surgical procedure while still maintaining accurate imaging. For example, a spatial mapping camera, when operating alone, may need to be placed or fixed at a location that is about 60-80 cm from the surgical procedure to maintain accuracy. However, the combination of the spatial mapping camera 300 and infrared or stereotactic camera 350 may be placed or fixed at a location that is about 1 meter away from the surgical procedure, thus providing a less cluttered surgical workspace that enables a surgeon more working freedom during the procedure and reduces the potential for contamination, with the cameras 300 and 350 a greater distance from the surgical procedure.

The mixed reality system 100 may also include an alignment jig 500 that can be secured to the exposed bone 400, or other desired anatomy. The jig 500 may include a first marker 502 which may be attached to the jig 500 at a fixed location on the bone 400. The first marker 502 may be a fiducial ball or other small identifier. Due to the high accuracy and resolution of the infrared or stereotactic camera 350, a small fiducial-type marker may be all that is necessary to clearly and accurately identify a desired location for the jig 500 on the bone 400, or a desired location of the surgical procedure on a bone 400 or other part of the anatomy. The jig 500 may also include a second marker 510 that may be moveable with respect to the jig 500 and the bone 400. The second marker 510 may also include a fiducial-type marker. The size and features of a fiducial ball or fiducial marker are well known in the art, and are particularly advantageous during surgical procedures due to the size, for example 3.5 cm in diameter, or less, or more, if desired.

Figure 2:
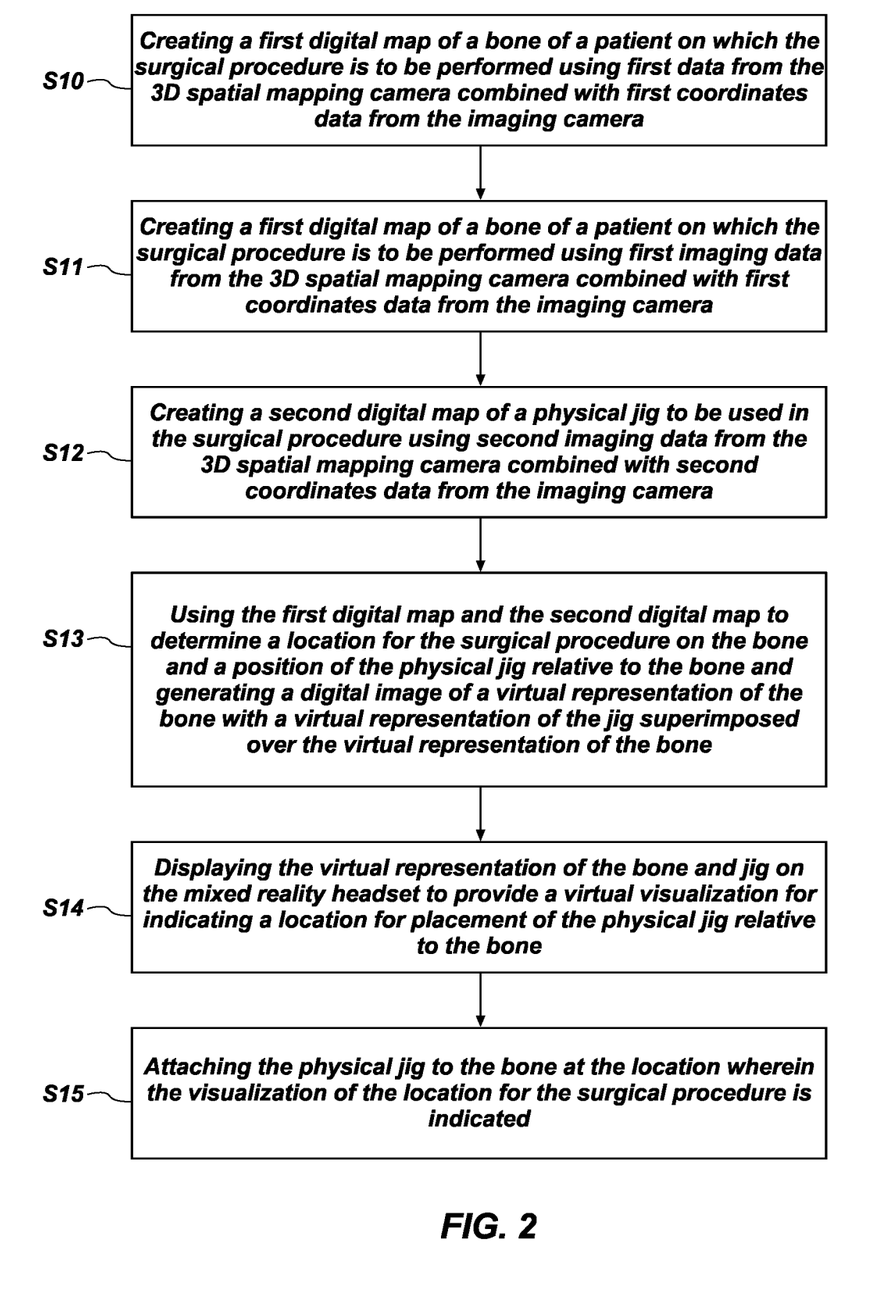
FIG. 2 is a flow diagram illustrating a method of using the mixed reality system.

FIG. 2 illustrates a flow diagram, used to show the method of using the mixed reality system 100 according to an exemplary embodiment. The system 100 in a first step S10, provides the computer system 200 connected to each of the mixed reality headset 102, 3D spatial mapping camera 300 and imaging camera 350, the computer system 200 configured to send display data to the mixed reality headset 102, and receive imaging data from the 3D spatial mapping camera 300 and the imaging camera 350.

The next step S11 includes creating a first digital map of the bone 400 of a patient on which the surgical procedure is to be performed using first imaging data from the 3D spatial mapping camera 300 combined with first coordinates data from the imaging camera 350. Then in the next step S12, the system 100 creates a second digital map of a physical jig 500 to be used in the surgical procedure using second imaging data from the 3D spatial mapping camera 300 combined with second coordinates data from the imaging camera 350.

Then in the next step S13 the system 100, uses the first digital map and the second digital map to determine a location for the surgical procedure on the bone 400 and a position of the physical jig 400 relative to the bone 500 and generates a digital image of a virtual representation of the bone 400 with a virtual representation of the jig superimposed over the virtual representation of the bone.

The system 100 in the next step S14 displays the virtual representation of the bone and jig on the mixed reality headset to provide a virtual visualization for indicating a location for placement of the physical jig relative to the bone, and then in the final step S15, the surgeon can attach the physical jig 500 to the bone 400 at the location wherein the visualization of the location for the surgical procedure is indicated.

Figure 3:
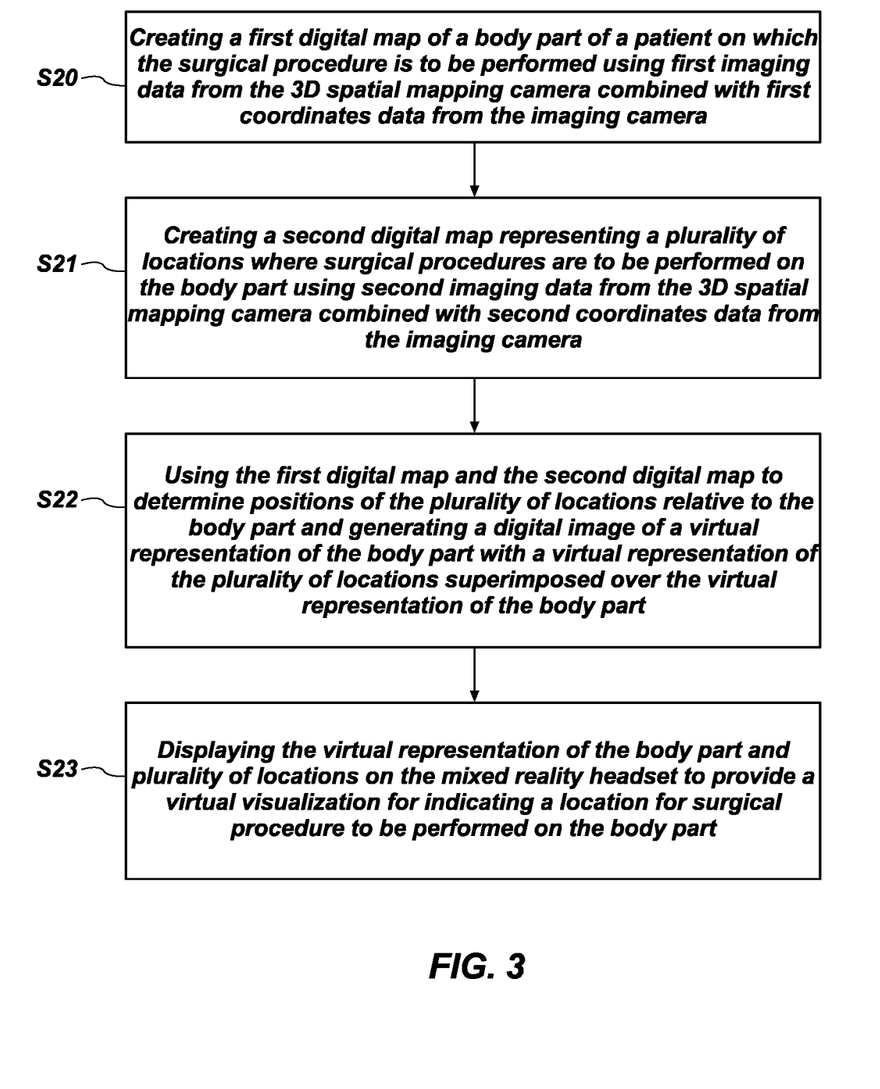
FIG. 3 is a flow diagram illustrating another method of using the mixed reality system.

FIG. 3 illustrates a flow diagram, used to show the method of using the mixed reality system 100 according to another exemplary embodiment. The system 100 in a first step S20 creates a first digital map of a body part of a patient on which the surgical procedure is to be performed using first imaging data from the 3D spatial mapping camera 300 combined with first coordinates data from the imaging camera 350. The in the next step S21, the system 100 creates a second digital map representing a plurality of locations where surgical procedures are to be performed on the body part using second imaging data from the 3D spatial mapping camera 300 combined with second coordinates data from the imaging camera 350.

In a next step S22 the system 100 uses the first digital map and the second digital map to determine positions of the plurality of locations relative to the body part and generating a digital image of a virtual representation of the body part with a virtual representation of the plurality of locations superimposed over the virtual representation of the body part.

And then the system in a final step S23, can display the virtual representation of the body part and plurality of locations on the mixed reality headset to provide a virtual visualization for indicating a location for surgical procedure to be performed on the body part.

FIG. 3 illustrates a schematic view of a perspective through the viewer 104 of the mixed reality headset 102, representing the view of a wearer of the mixed reality headset 100 during a procedure. As shown, the view can display a visualization of a jig or a virtual jig 550 overlaid on the actual physical bone 400, enabling the wearer to see or view a virtual jig 550 simultaneously with the bone 400, after utilizing the system methodology of FIG. 2 or 3.

Figure 4:
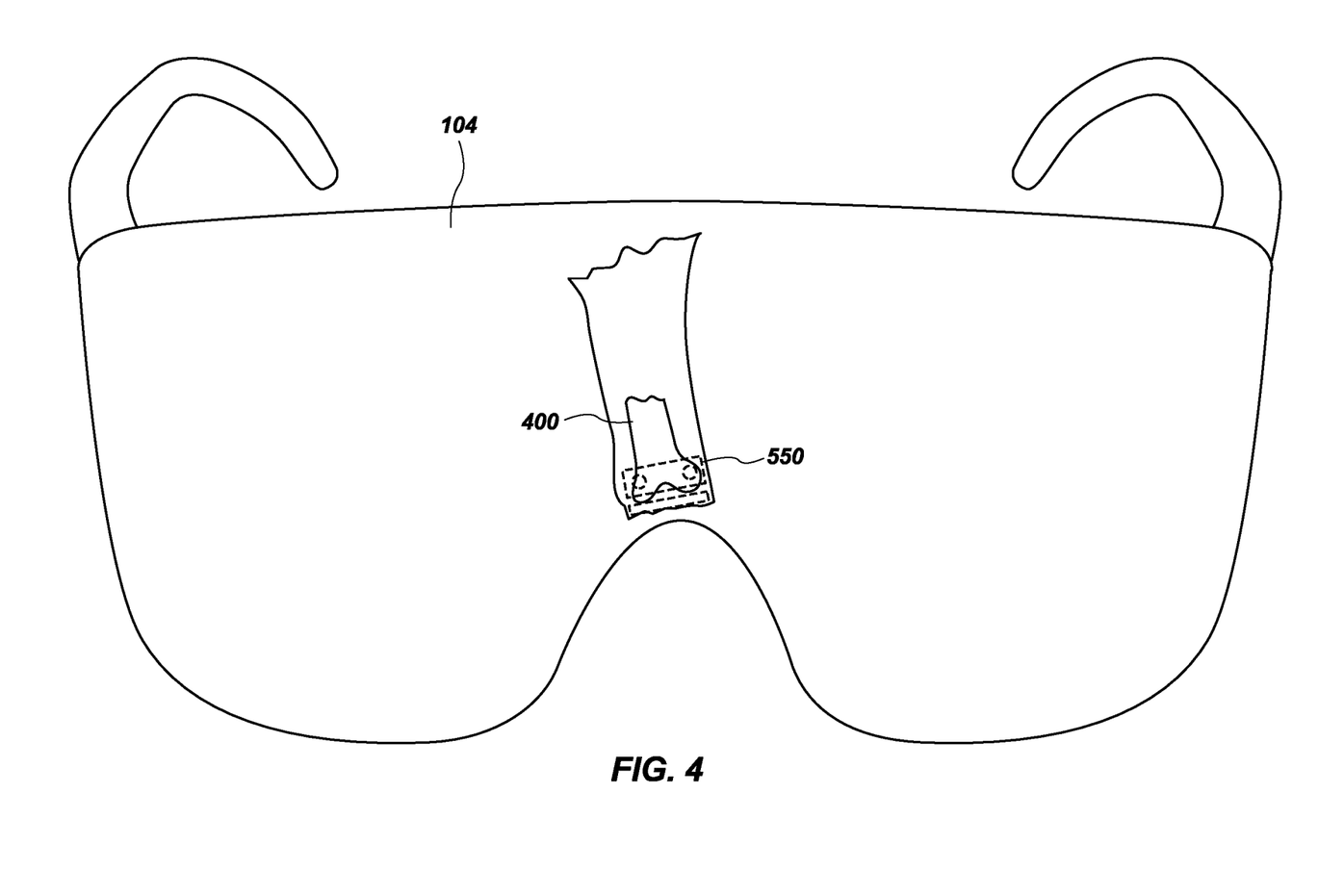
FIG. 4 is a perspective view of another embodiment of a mixed reality system of the present disclosure.
Figure 5:
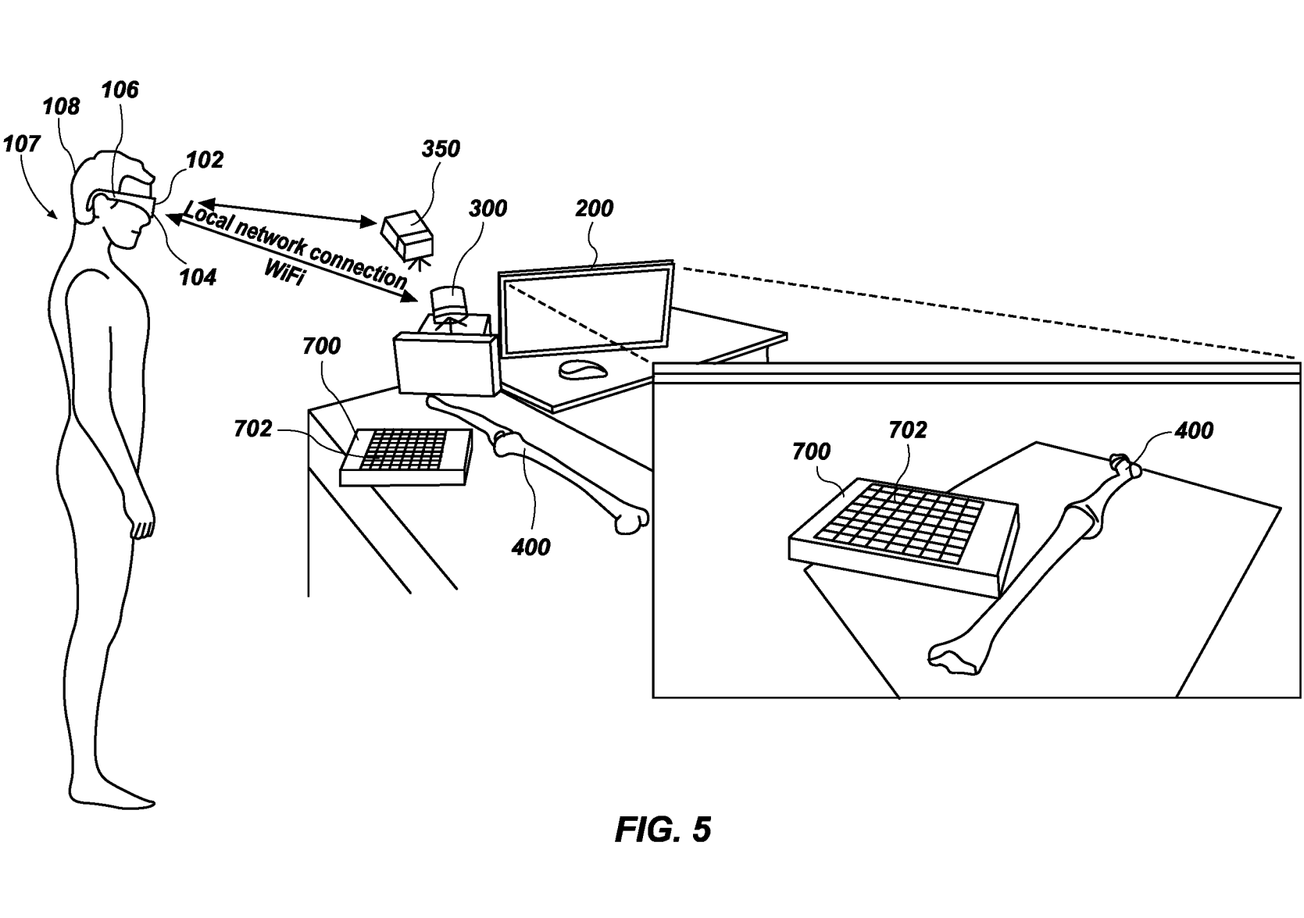
FIG. 5 is a schematic rendering of a view through a mixed reality display of a further embodiment of the present disclosure.

In another embodiment, as shown in FIG. 4, the headset 102, the spatial mapping camera 300 and the infrared or stereotactic camera 350 may utilize a physical calibration tool 700 to calibrate and align 3D coordinates with the 3D contours of the exposed bone 400 or anatomy. The calibration tool 700 may include a specially designed calibration pattern 702 that may be scanned by the headset 102 and/or the spatial mapping camera 300, and/or the infrared or stereotactic camera 350, which can then send the corresponding calibration data to the computer system 200 which can then use the calibration data to provide accurate coordinates to the headset 102 to identify where to drill, cut, or otherwise prepare the bone 400.

Using the mixed reality system 100, a surgeon or user may perform a surgical procedure by first exposing the bone 400, or other desired anatomy. The spatial mapping camera 300 may then continuously 3D spatially map the exposed bone 400, and send the corresponding image data or mapping information to the computer system 200. In alternative embodiments, multiple spatial mapping cameras 300 may be used in unison, to provide more accurate and expansive imaging.

A surgeon or user may then substantially simultaneously, or before, or after, the 3D mapping, identify coordinates on the exposed bone 400 identifying a desired placement of the jig 500 or surgical procedure by using the infrared or stereotactic camera 350, and send the corresponding coordinate information to the computer system 200. In alternative embodiments, multiple infrared or stereotactic cameras 350 may be used in unison to provide more accurate and expansive imaging.

The surgeon may then attach the jig 500 to the exposed bone 400 at a predetermined or desired location. The spatial mapping camera 300 may spatially map, and the infrared or stereotactic camera may identify coordinates of, the jig 500 and the exposed bone 400 to map the surface of the exposed bone and relative location of the jig 500.

Figure 6:
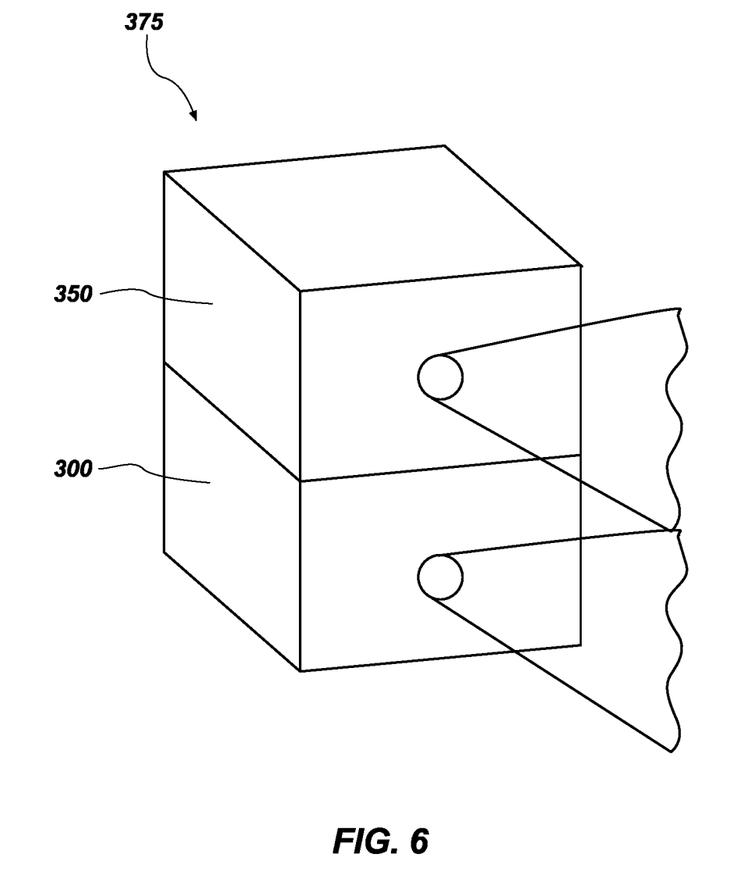
FIG. 6 is a schematic view of a combined unitary camera structure.

As shown in FIG. 6, the 3D spatial mapping camera 300 and the infrared or stereotactic camera 350 may be formed as a combined unitary structure 375. This unitary structure 375 may permanently fix cameras 300 and 350 relative to one another, or enable cameras 300 and 350 to be removably connected to one another. This combined structure or device may increase the portability of the cameras 300 and 350, which in some circumstances may increase efficiency of an operation or surgical procedure. As shown in FIG. 1, however, cameras 300 and 350 may also be placed or fixed at separate locations in an operating room or other desired space.

Figure 7:
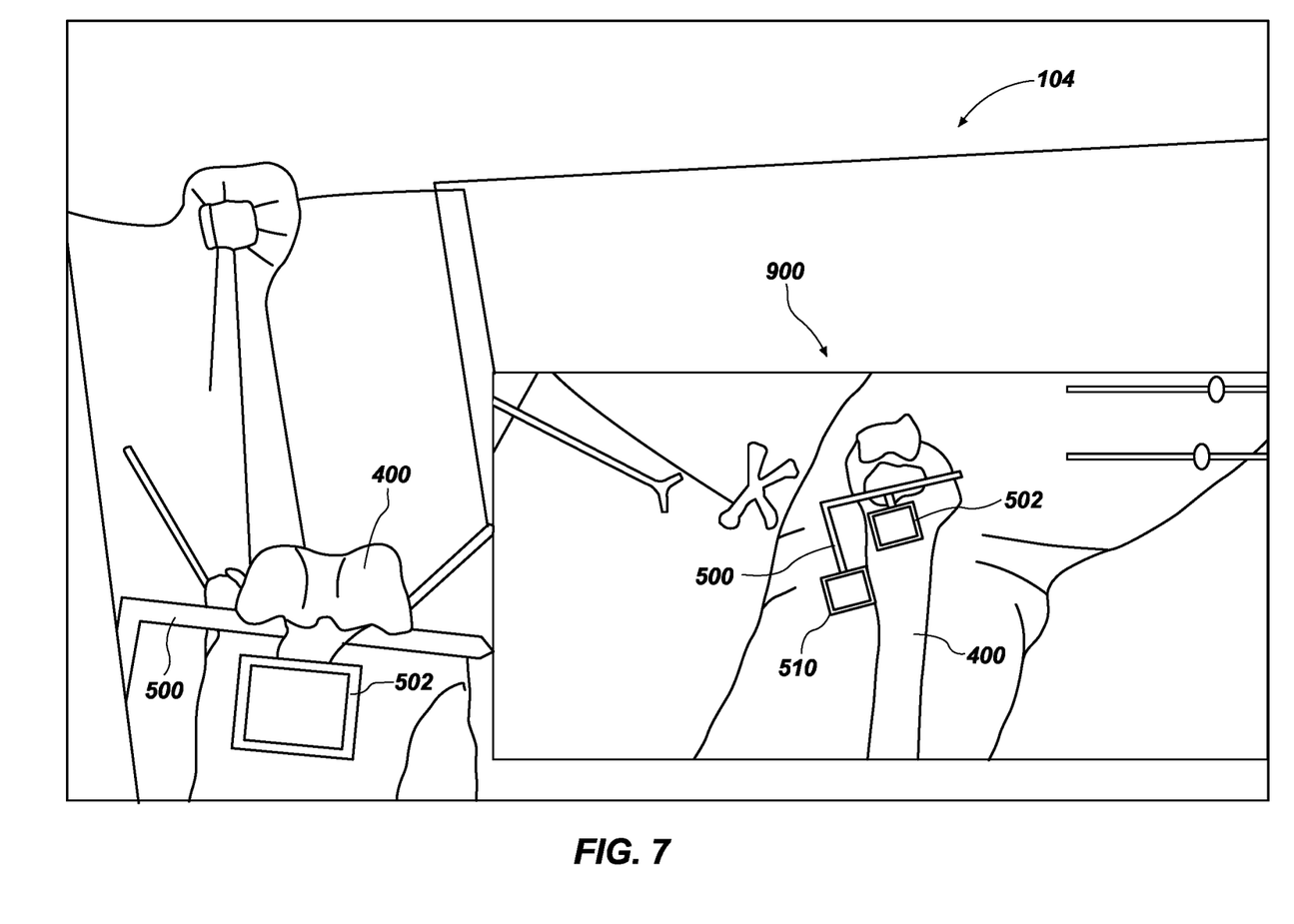
FIG. 7 is a front view of a user perspective of a mixed reality headset viewer of the present disclosure.

As shown in FIG. 7, the headset 102 may generate a holographic image 900, or visual representation, viewable by the surgeon on the viewer 104, such that the surgeon can maintain a real-world view of the bone 400 and simultaneously view the holographic image 900. The holographic image 900 may include a real-time rendering or visual representation of the exposed bone 400 and a real-time rendering or visual representation of the jig 500. The headset 102 can then scan one or both of the markers 502 or 504 and identify the proper or required position of the jig 500, relative to the bone 400. The surgeon can then manipulate the jig 500, until the proper position is set and determined.

Once the proper position of the jig 500 is set in the holographic image 900, the surgeon can use the headset 102 to lock the holographic image 900 in place. Then the surgeon can manipulate the actual physical jig 500 to substantially match the positioning of the set rendering of the jig 500.

Figure 8:
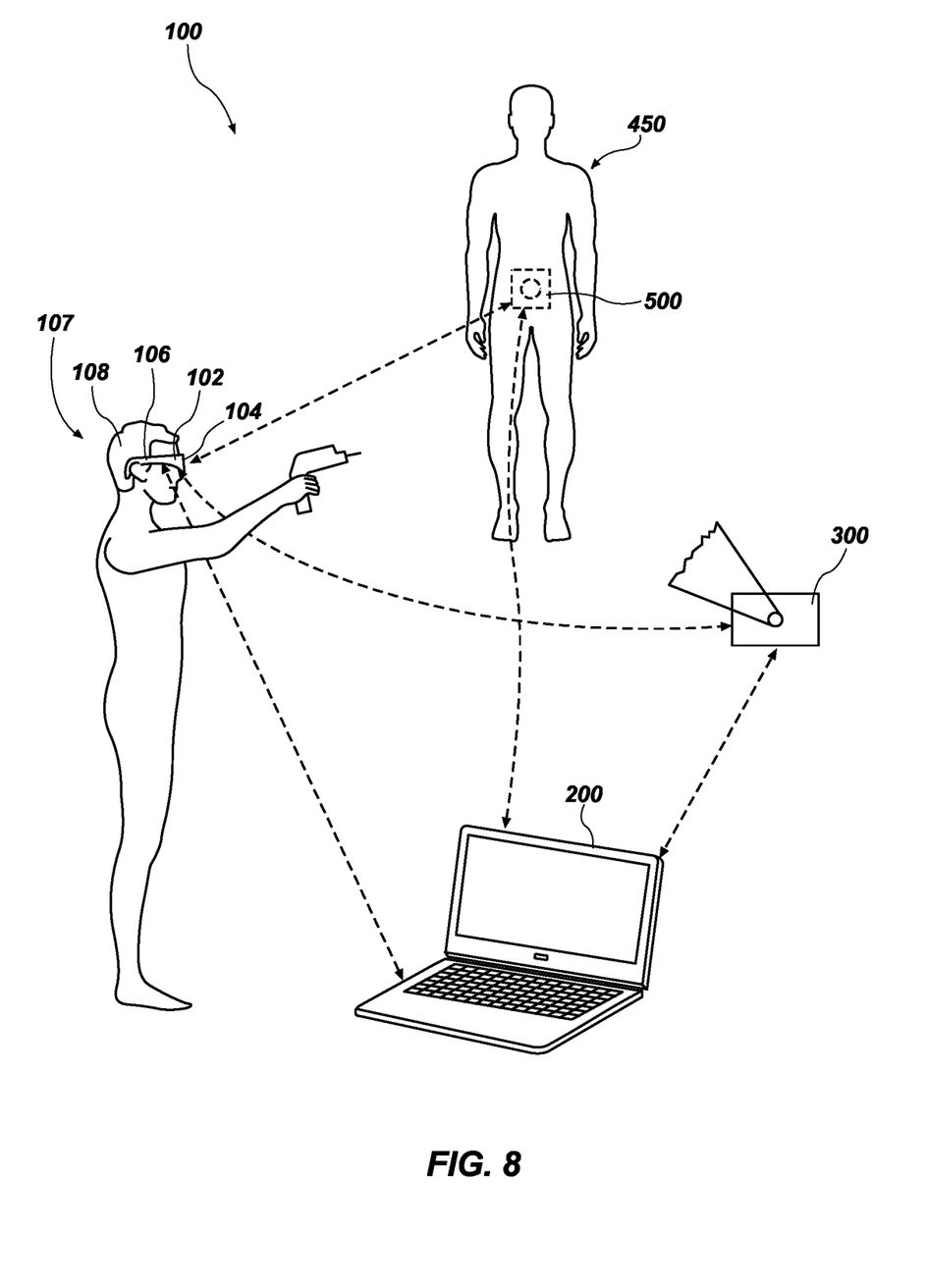
FIG. 8 is schematic rendering of another mixed reality system of the present disclosure.

In another embodiment, as shown in FIG. 8, the mixed reality system 100 may be used such that one of the cameras 300 or 350 may be utilized outside of a patient's body 450, while another one of the cameras 300 and 350 may be inserted within the patient's body to spatially map or identify coordinates for a surgical procedure from within the body. Alternatively, the system 100 may use multiple 3D spatial mapping cameras 300, e.g., one or more spatial mapping cameras on the exterior of the patient and one or more additional spatial mapping cameras on the interior of the patient. The combined images of the camera 300 or 350 outside of the patient's body, and the camera 300 or 350 inside the patient's body may provide more accurate data for identifying the location of a surgical procedure. For example, camera 300 or 350 may be inserted into a patient's lungs, throat, stomach, colon, vagina, rectum, or any other desired cavity or interior space within a patient's body. The image information of the inside and outside cameras 300 and 350 can then be superimposed as described above to provide additional detail and location orientation that are not otherwise available from imaging only outside the body. As an additional example, a surgeon can use the imaging information from the two or more cameras 300 or 350 to then identify a surgical procedure location within the patient, and such location could be marked or "tattooed" and then a surgeon could then more easily locate the marked location during the surgical procedure, e.g., using a laparoscope or other similar surgical device.

A surgical jig is conventionally, and may be, a surgical tool that may be used to help a surgeon make predetermined and accurate cuts of a desired bone to facilitate attachment of a surgical implant. A jig may have one or a series of slots located at specific predetermined locations and at specific predetermined angles, with respect to a body of the jig, such that when the jig is attached to a bone surface. The surgeon can make precise and accurate cuts using the jig as a guide without the need of additional measurements. Once the desired cuts of the bone have been made using the jig as a guide, the jig may be removed from the bone and the surgical implant may be properly secured to the bone, which has now been accurately cut to receive the implant.

Due to the accuracy of the disclosed method and system, the jig 500 may be made of plastic, metal, polyamide, or any other desired material. Manufacturing the jig 500 out of a plastic or polyamide material, or other relatively inexpensive material, may allow the jig 500 to be disposable, while still maintaining the precision and accuracy of traditional metal jigs. The jig 500 may also be manufactured using a 3D printer, which can further reduce the cost of manufacturing and storage of jigs, since 3D printed jigs could be made on demand and customized to the size and shape required by individual patients and users. The physical jig 500 may also be manufactured using any other known technique for forming a physical jig.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed:

1. A system for determining a location for a surgical jig in a surgical procedure, comprising:
    a jig configured and arranged to be fixed to a bone;
    a mixed reality headset;
    a 3D spatial mapping camera configured to map the bone and the jig;
    an imaging camera configured to identify coordinates of a desired location; and
    a computer system configured to transfer data to and from the mixed reality headset, the 3D spatial mapping camera, and the imaging camera, and further configured to identify a location for the surgical procedure, wherein the mixed reality headset is configured to provide a visualization of the location for the surgical procedure using the data combined from the 3D spatial mapping camera and the imaging camera.

2. The system of claim 1, wherein the mixed reality headset is configured to provide a virtual jig and a virtual bone, which are representations of the jig and bone, and enable a user to manipulate the location of the virtual jig as viewed in the mixed reality headset, with respect to the virtual bone.

3. The system of claim 1, wherein the mixed reality headset is configured to provide a virtual jig and a virtual bone and enable a user to fix a location of the virtual jig as viewed in the mixed reality headset, with respect to the virtual bone, and manipulate the location of the jig with respect to the bone, to substantially match the location of the virtual jig with respect to the virtual bone.

4. The system of claim 1, wherein the jig includes a marker configured to be scanned by the mixed reality headset to provide data relating to the location of the jig.

5. The system of claim 4, further comprising:
    wherein the imaging camera is configured to scan the marker of the jig, and identify a position of the jig with respect to the bone based, at least in part, on the data provided by scanning the marker.

6. The system of claim 5, wherein the marker is a fiducial marker.

7. The system of claim 1, wherein the imaging camera and the spatial mapping camera are placed in locations separate from one another.

8. The system of claim 1, wherein the imaging camera and the spatial mapping camera are formed as a combined unitary structure.

9. The system of claim 1, wherein the imaging camera is a stereotactic camera.

10. The system of claim 1, wherein the imaging camera is an infrared camera.

11. The system of claim 1, wherein the mixed reality headset is separate and not mechanically connected to the 3D spatial mapping camera or the imaging camera.

12. A system for determining a location for a surgical jig in a surgical procedure, comprising:
    a jig configured and arranged to be fixed to a bone;
    a mixed reality headset;
    a first imaging camera configured to map the bone and the jig;
    a second imaging camera configured to identify coordinates of a desired location; and
    a computer system configured to transfer data to and from the mixed reality headset, the first imaging camera, and the second imaging camera, and further configured to identify a location for the surgical procedure, wherein the mixed reality headset is configured to provide a visualization of the location for the surgical procedure using the data combined from the first imaging camera and the second imaging camera.

13. The system of claim 12, wherein the mixed reality headset is configured to provide a virtual jig and a virtual bone, which are representations of the jig and bone, and enable a user to manipulate a location of the virtual jig as viewed in the mixed reality headset, with respect to the virtual bone.

14. The system of claim 12, wherein the mixed reality headset is configured to provide a virtual jig and a virtual bone and enable a user to fix a location of the virtual jig as viewed in the mixed reality headset, with respect to the virtual bone, and manipulate the location of the jig with respect to the bone, to substantially match the location of the virtual jig with respect to the virtual bone.

15. The system of claim 12, wherein the jig includes a marker configured to be scanned by the mixed reality headset to provide data relating to the location of the jig.

16. The system of claim 15, wherein the second imaging camera is configured to scan the marker of the jig, and identify a position of the jig with respect to the bone based, at least in part, on the data provided by scanning the marker.

17. The system of claim 12, wherein the mixed reality headset is further configured to continuously provide a visualization of the location for the surgical procedure, throughout the surgical procedure, using a continuously generated digital map generated by the first imaging camera and continuously generated coordinates generated by the second imaging camera.

18. The system of claim 12, wherein the first imaging camera and the second imaging camera are placed in location separate from one another.

19. The system of claim 12, wherein the first imaging camera and the second imaging camera are formed as a combined unitary structure.

20. The system of claim 12, wherein the first imaging camera is a 3D spatial mapping camera.

21. The system of claim 12, wherein the second imaging camera is a stereotactic camera.

22. The system of claim 12, wherein the second imaging camera is an infrared camera.

23. The system of claim 12, wherein the mixed reality headset is separate and not mechanically connected to the first imaging camera or the second imaging camera.

24. A system for determining a location for a surgical jig in a surgical procedure, comprising:
   a jig configured and arranged to be fixed to a bone; a mixed reality headset;
   a first imaging camera configured to map the bone and the jig;
   an infrared camera configured to identify coordinates of a desired location; and
   a computer system configured to transfer data to and from the mixed reality headset, the first imaging camera, and the infrared camera, and further configured to identify a location for the surgical procedure, wherein the mixed reality headset is configured to provide a visualization of the location for the surgical procedure using the data combined from the first imaging camera and the infrared camera.

25. The system of claim 24, wherein the mixed reality headset is configured to provide a virtual jig and a virtual bone, which are representations of the jig and bone, and enable a user to manipulate a location of the virtual jig as viewed in the mixed reality headset, with respect to the virtual bone.

26. The system of claim 24, wherein the mixed reality headset is configured to provide a virtual jig and a virtual bone and enable a user to fix a location of the virtual jig as viewed in the mixed reality headset, with respect to the virtual bone, and manipulate the location of the jig with respect to the bone, to substantially match the location of the virtual jig with respect to the virtual bone.

27. The system of claim 24, wherein the jig includes a marker configured to be scanned by the mixed reality headset to provide data relating to the location of the jig.

28. The system of claim 27, wherein the infrared camera is configured to scan the marker of the jig, and identify a position of the jig with respect to the bone based, at least in part, on the data provided by scanning the marker.

29. The system of claim 24, wherein the first imaging camera is a 3D spatial mapping camera.

30. A system for determining a location for a surgical jig in a surgical procedure, comprising:
   a jig configured and arranged to be fixed to a bone; a mixed reality headset;
   a first imaging camera configured to map the bone and the jig;
   an infrared camera configured to identify coordinates of a desired location; and
   a computer system configured to transfer data to and from the mixed reality headset, the first imaging camera, and the infrared camera, and further configured to identify a location for the surgical procedure, wherein the mixed reality headset is configured to provide a visualization of the location for the surgical procedure using the data combined from the first imaging camera and the infrared camera, wherein the mixed reality headset is separate and not mechanically connected to the first imaging camera or the second imaging camera; wherein the mixed reality headset is configured to provide a virtual jig and a virtual bone, which are representations of the jig and bone, and enable a user to manipulate the location of the virtual jig as viewed in the mixed reality headset, with respect to the virtual bone, wherein the jig includes a marker configured to be scanned by the mixed reality headset to provide data relating to the location of the jig and wherein the marker is a fiducial marker; wherein the second imaging camera is configured to scan the marker of the jig, and identify a position of the jig with respect to the bone based, at least in part, on the data provided by scanning the marker; wherein the first imaging camera and the second imaging camera are formed as a combined unitary structure; wherein the first imaging camera is a 3D spatial mapping camera; and
wherein the second imaging camera is an infrared camera.

* * * * *